United States Patent [19]
Rooks

[11] Patent Number: 5,904,684
[45] Date of Patent: May 18, 1999

[54] DEVICE AND METHOD FOR SIMULTANEOUS BILATERAL PELVIC OSTEOTOMIES

[76] Inventor: Robert L. Rooks, 1912 Pine Ave., Huntington Beach, Calif. 92648-2761

[21] Appl. No.: 08/842,725

[22] Filed: Apr. 16, 1997

[51] Int. Cl.$^6$ .................................................. A61B 17/80
[52] U.S. Cl. ........................................... 606/69; 606/101
[58] Field of Search ............................ 606/101, 69, 70, 606/71, 86, 72, 73, 53, 60

[56] References Cited

U.S. PATENT DOCUMENTS

| | | |
|---|---|---|
| Re. 28,841 | 6/1976 | Allgower et al. . |
| 643,773 | 2/1900 | Metcalf . |
| 1,704,883 | 3/1929 | Cullinan . |
| 2,413,362 | 12/1946 | Maxwell . |
| 2,737,835 | 3/1956 | Herz ........................................ 606/101 |
| 3,824,995 | 7/1974 | Getscher et al. . |
| 3,854,268 | 12/1974 | Gutner . |
| 4,120,298 | 10/1978 | Fixel . |
| 4,384,802 | 5/1983 | Lo et al. . |
| 4,393,568 | 7/1983 | Navarro . |
| 4,454,876 | 6/1984 | Mears . |
| 4,479,491 | 10/1984 | Martin . |
| 4,762,122 | 8/1988 | Slocum . |
| 4,800,874 | 1/1989 | David et al. . |
| 5,674,222 | 10/1997 | Berger et al. .............................. 606/69 |

FOREIGN PATENT DOCUMENTS 0100114  7/1982  European Pat. Off. .

OTHER PUBLICATIONS

Robert B. Salter (1961). The Classic Innominate Osteotomy in the Treatment of Congenital Dislocation and Subluxation of the Hip.
George T. Rab, (1970) Biomechanical Aspects of Salter Osteotomy.
Campbell's Operative Orthopaedics (1971) Congenital Dysplasia/Hip.
H.J. Straub (1973) Chiari Pelvic Osteotomy for Hip Dysplasia in Patients Below the age of 20.
David H. Sutherland (1974) Double Innominate Osteotomy.
William P Barret et al (1986) The Effectiveness of the Salter Innominate Osteotomy in the Treatment of Congenital Dislocation.
Major Paul C. Perlik (1985) A Combination Pelvic Osteotomy for Acetabular Dysplasia in Children.
Lynn T. Staheli(1990) Surgical Management of Acetabular Dysplasia.
M.A.P. Kooijman (1990) Triple Osteotomy of the Pelvis.
William S.Smith (1963) Etiology of Congenital Dislocation of Hip.

(List continued on next page.)

*Primary Examiner*—Guy V. Tucker
*Attorney, Agent, or Firm*—Curtis L. Harrington

[57] ABSTRACT

A method and device facilitates the procedure of a transverse osteotomy of both ilium and a secondary osteotomy through the pelvic symphysis. A plate is utilized which has facility for attachment of eight screws into the, animal bone tissue to more securely hold the plate in place. The shape of the plate represents a significant advance and has important characteristics, including (1) only one side of the plate has sharply angled surfaces to accommodate rotated pelvic bone portions, the other side of the plate is smoothly continuous and facilitates a more stable direct insertion of the bone screws to prevent non-even pressure from being applied to the bores provided for insertion of the bone screws; (2) In this configuration, the bores can closely match the shapes of the heads of the bone screws and provide less exposed material at the outside of the plate, as well as providing entry of bone screws at right angles to the bone tissue adjacent the sharply angled surfaces; (3) the plate provides the ability for it to be bent and, more than ample material is provided to bend the plate along its axis to provide an even more enhanced ability to insert bone screws at right angles to the extent of the pelvic bone tissue and to avoid an angle which would prevent secure bone attachment of the bone screws and maximum surface area contact and support from the sharply angled surfaces directly onto bone tissue.

20 Claims, 6 Drawing Sheets

OTHER PUBLICATIONS

Wayne H. Riser et al (1966) Hip Dysplasia: Coxofemoral Abnormalities in neonatal German Sherherd Dogs.

B. Henricson et al (1966) On the Etiology and Pathogenesis of Hib Dysplasia: A comparitive Review.

S. Paatsama et al (1966) Arthroplasty of the Dysplastic Canine Hip Joint.

R. Bruce Hohn et al (1969) Clinical Orthopaedics and Related Re–earch–Pelvic Osteotomy inthe Treatment of Canine Hip Dysplasia.

Donald L. Pietmattei (1971) The Veterinary clinics of North America Symposium on Orthopedic Surgery in Small Animals, Corrective Osteotomy Procedures for Treatment of Canine Hip Dysplasia.

Wade O. Brinker (1971) Corrective Osteotomy Procedures for Treatment of Canine Hip Dysplasia.

Veterinary Pathology (1975) Growth and Development of the Normal Canine Pelvis, Hip Joints and Femer from Birth to Maturity.

M.Joseph Bojrab (1975) Current Techniques in Small Animal Surgery, Pelvic Osteotomy.

Steven P. Arnoczky et al (1981) Biomechanical Analysis of Forces Acting About the Canine Hip.

Gerald J. Pijanowski, et al (1981) In Vitro Analysis of Two Canine Pelvic Osteotomy Techniques. Veterinary Surgery 10(4).

Steven C. Schrader (1981) A triple Osteotomy of the Pelvis as a Treatment for Canine Hip Dysplasia: A Preliminary Report.

N. Bohler et al (1983) Guidelines for Chiari's Osteotomy in the Immature Skeleton Developed from a Canine Model.

Wade O. Brknker et al (1983)Handbook of Small Animal Orthopedics & Fracture Treatment, Lameness and Joint Surgery, Hip Dysplasia.

M.Joseph Bojrab et al(1983) Current Techniques in Small Animal Surgery, Pelvic Limp, Corrective Osteotomies for Treatment of Selected Hip Joint Disorders.

Barclay Slocum et al, (1985) Pelvic Osteotomy Techinque for Axial Rotation of the Acetabular Segment in Dogs.

J.W. Alexander (1985) Leonard's Orthopedic Surgery of the Dog and Cat, Hip Dysplasia.

Douglas H. Slatter, (185)Textbook of Small Animal Surgery, Osteotomies of the Hip.

G.Sumner–Smith (1988) Decision Making in Small Animal Orthopaedic Surgery, Canine Hip Dysplasia.

Charles D. Newton et al (1988) Textbook of Small Animal Orthopaedics, Osteotomy of the Pelvis.

Steven C. Schrader (1986) JAVMA, Triple Osteotomy of the Pelvis and trochanteric Osteotomy as a Treatment for Hip Dysplasis in the immature dog: The surgical Technique and results of 77 consecutive operations.

C.A. Hunt et al (1988) Stabilization of Canine Pelvic Osteotomies with AO/ASIF Plates and Screws.

William G. Hitttick (1990) Canine Orthopedics, Pelvic Osteotomy, Pathomechanics of Hip Dysplasia.

Wade O. Brinker(1990) Handbook of Small Animal Orthopedics & Fracture Treatment, Hip Dysplasia, Part II Lameness and Joint Surgery.

M. Joseph Bojrab (1990) Current Techniques in Small Animal Surgery, Pelvic Limb, Pelvic Osteotomy.

Ron M. McLaughlin (1991)Veterinary Surgery, Force Plate Analysis of Triple Pelvic Osteotomy for the Treatment of Canine Hip Dysplasia.

Steven C Schrader (1992) Reports of Retrospective Studies, Pelvic Osteotomhy as a Treatment for Obstipation in cats with acquired stenoses of the pelfic canal: Six cases (1978–1989).

Gary L Ailes (no year) Acetabular Translocation/Diala hip.

Ron McLauglin Jr. (no year) Force Plate Gait Analysis of Triple Pelvic Osteotomy for the Treatment of Canine Hip Dysplasia.

Gregory M.Zolton. (no year) A review of 23 Bilateral Triple Pelvic Osttotomies.

Graehler (no year) The effects of Ilial Osteotomies and Axial Rotation of the Structural Anatomy of the Pelvis.

No Author, (no year) Management of Canine Hip Dysplasia.

Hans G. Luhr, (1992) Specifications, Indications, and Clinical Applications of the Luhr Vitallium Maxillofacial Systems.

Marshall R. Urist (1974), Clinical Orthopaedics and Related Research.

Douglas W. McKay, (no date) Classification of Pelvic Osteotomies: Principles and Experiences.

Dietrich Tonnis, (no date) Triple Osteotomy Close to the Hip Joint.

Howard H. Steel, (no date) Triple Osteotomy of the Innominate Bone.

Short Abstract 1, by Rooks, R. L., Zolton, G.M., Khachatoorian, L.B. "A Comparison of 2 Techinques for Simultaneous Bilateral Pelvic Osteotomies: Results of 90 Cases", Oct. 31, 1995.

Short Abstract 2, by Rooks, R. L., Blackwood, K., Khachatoorian, L.B. A Comparison of Surgical Complications for Pelvic Osteotomy Fixation Using a 6–hole Canine Pelvic Osteotomy Plate and an 8 Hole Biplanar Osteotomy Plate.

Richards Manufacturing brochure, "Jewett Benders", 1 page. Author unknown, Jul. 1953.

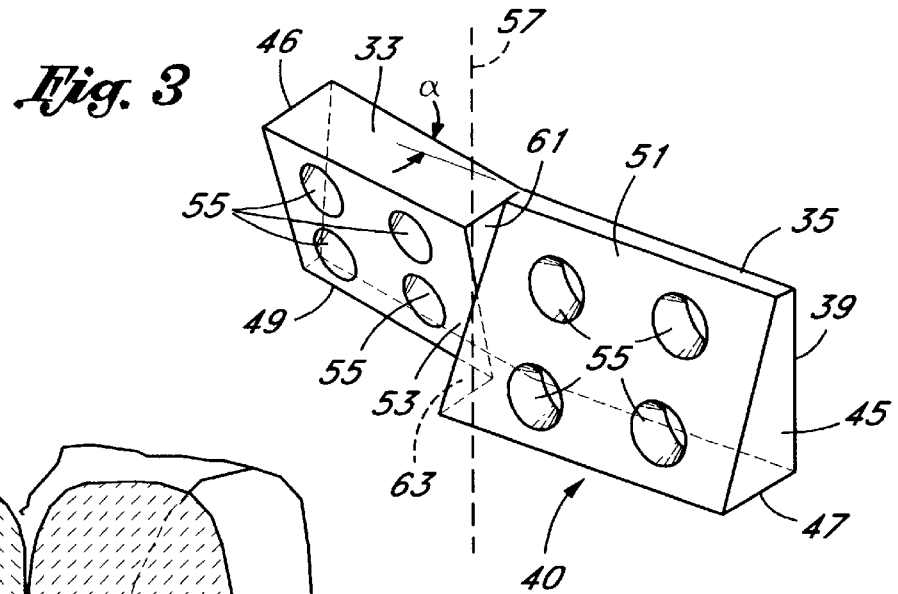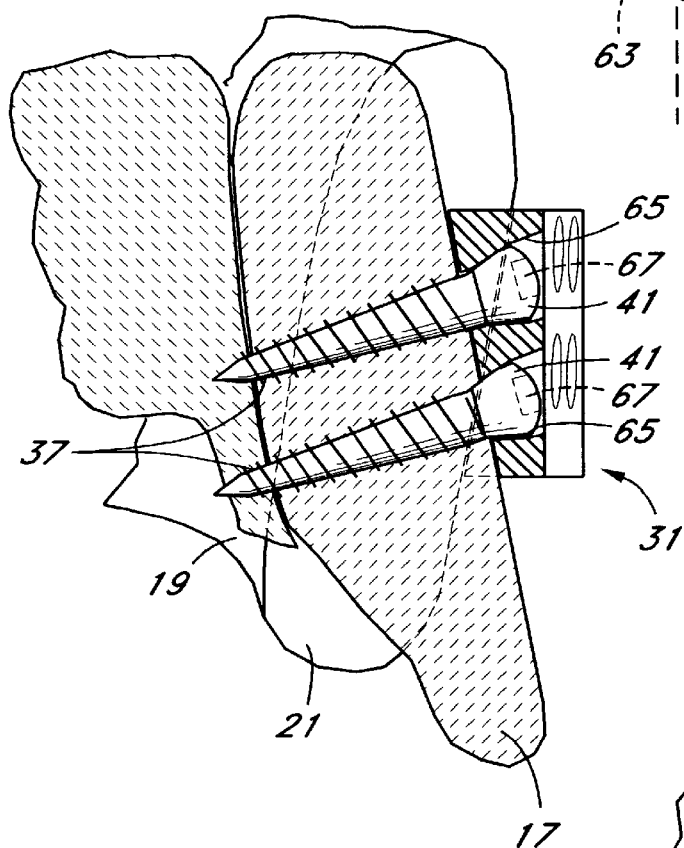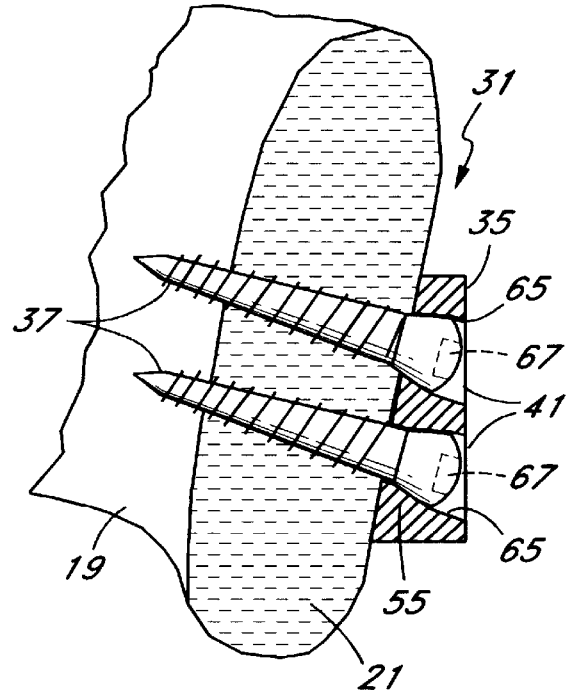

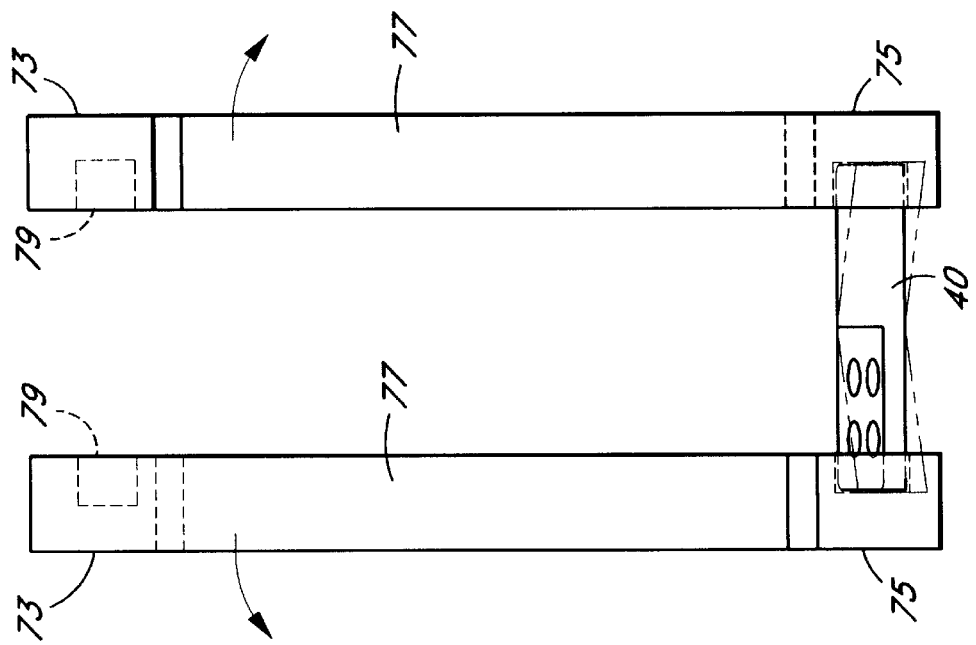
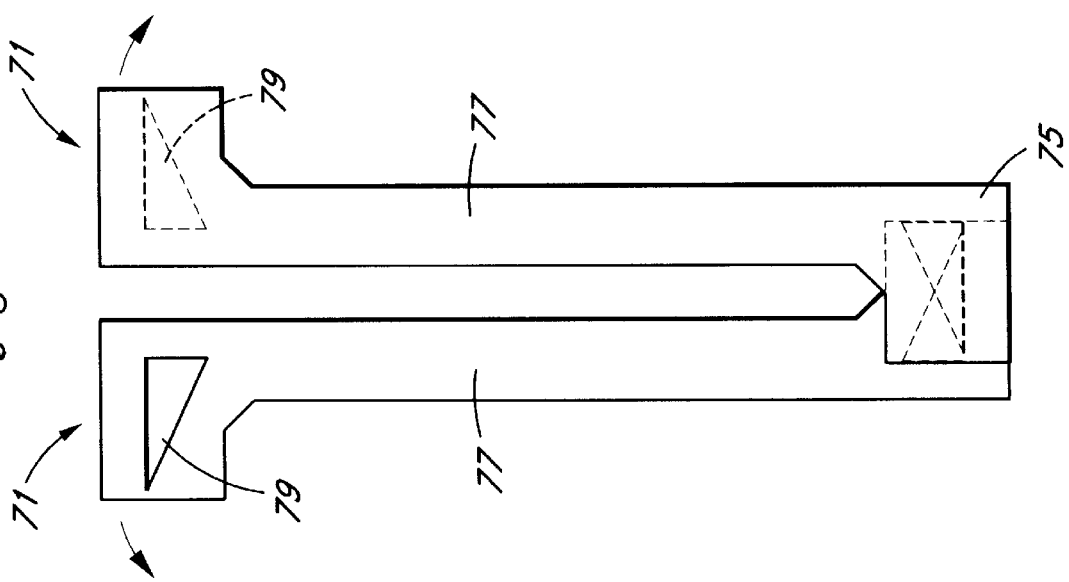
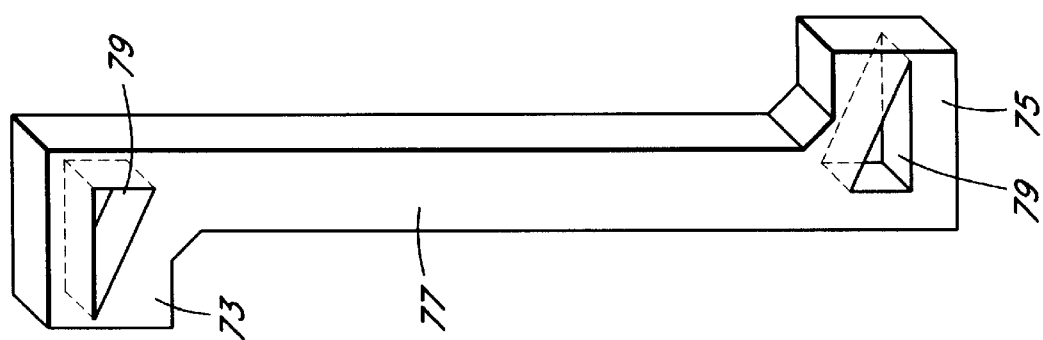

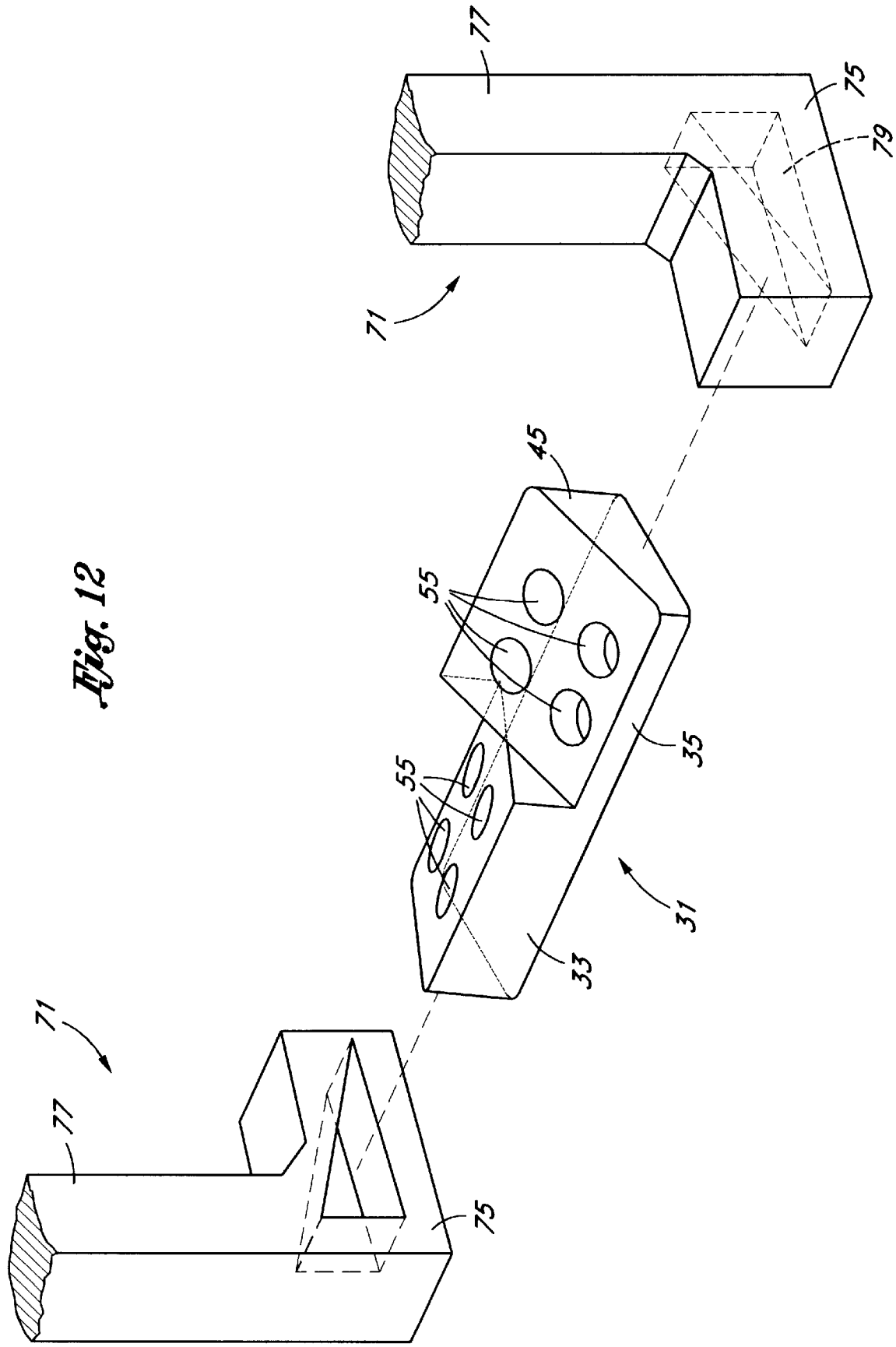

DEVICE AND METHOD FOR SIMULTANEOUS BILATERAL PELVIC OSTEOTOMIES

FIELD OF THE INVENTION

This invention relates to an improved osteotomy procedure and fixation plate particularly adapted to the procedure for correcting the animal pelvis, and which involves the transverse osteotomy of both ilia and a secondary osteotomy through the pelvis symphysis, as well as an improved plate for facilitating and improving the results of the procedure and which is modifiable both before and during the operative procedure to be highly customized to the configuration of a given animal pelvis.

BACKGROUND OF THE INVENTION

Canine hip dysplasia remains an important problem to be solved in general veterinary practice. In less severe cases, non-operative treatment can produce satisfactory results, but more severe cases require surgical intervention.

Hip dysplasia is a painful and often debilitating condition seen most frequently in canines and is the result of an instability between the acetabulum and the femoral head. It usually results from a genetic or congenital condition wherein the acetabulum, the cup-shaped socket within the pelvis which receives the femoral head, is insufficiently formed. When the femoral head is not properly covered by the insufficient acetabulum, as the joint bears weight there is instability and the potential of injury to the surrounding tissue.

The surgical techniques for correcting hip dysplasia are known as pelvic osteotomy. This procedure provides for osteotomy of selected bone segments of the pelvis followed by rotation of the acetabular segment of the pelvis to enable better coverage of the femoral head, in order to give the canine a full range of motion for the hind legs. Typical complications, besides those associated with any surgical technique, are loss of fixation and compromise of the pelvic inlet. The loss of fixation may leave the canine patient in a worse state than before the surgery because the procedure is quite invasive requiring three pelvic osteotomies, and requires the removal of one pelvic section and the separation and rotation of another. The compromised pelvic inlet may cause chronic bowel and urinary tract problems which may only be uncomfortable, but at worse may be injurious. When coupled with the neuroses that frequently accompany such invasive surgical techniques, these complications generally render this procedure seriously flawed.

Another surgical technique has more recently been developed which requires three planar cuts in the pelvis one through the pubic ramus, one through the tuber ischii, and one through the ilium. A pelvic side segment is created and rotation of the acetabular segment rotates the side segment. A plate is used to secure the pelvic side segment at one end, at the ilium. A wire connector is used at the ischii to hold the other end of the segment in place at an awkward angle.

U.S. Pat. No. 4,762,122 to Slocum discloses a six hole dual planar plate having an interconnecting orthogonal web which places the plates at a constant planar angle to each other. This six hole plate, when used in procedures according to Slocum involving the rotation of an acetabular segment, and also used in a more refined procedure which included a transverse osteotomy of both ilium and a secondary osteotomy through the pelvic symphysis, still resulted in loosened or broken screws securing the plate, and loss of bone purchase resulting in the necessity of replacing the plates.

As between the two techniques, the more refined technique of a transverse osteotomy of both ilium and a secondary osteotomy through the pelvic symphysis provides superior results, including a self ambulatory result within about 24 hours of surgery compared to about three days to a self ambulatory state with the ilial section rotation technique. The secondary osteotomy removes bone tissue to accommodate the resulting pelvic narrowing which occurs during rotation of the pelvic segments toward each other.

For a more accurate comparison, pelvic osteotomies were performed in 100 cases involving the more refined technique. It was found that the six hole plate of Slocum was problematic since the angles of the plates were fixed. Since the angles of the six hole plate are determined by the web shape, the angle of the plates could not be changed without either distorting the web shape or distorting the plates by producing a severe twist in their planes.

Further, complications for the six hole plate included broken screws, loosened screws and bilateral loss of bone purchase requiring replacement of screws. The problems encountered were related to the requirement in each case for an angular plate displacement differing from the displacement required for optimum pelvic placement. Also, the physical configuration and placement of the screws were not sufficient for bone retention. In cases where failure occurs, the results to the canine patient are severe. The requirement to surgically re-enter and perform further work is especially difficult on the animal, and requires a period of re-recovery.

Therefore, any technique or apparatus which reduces or eliminates the necessity to surgically re-enter the patient introduces a significant improvement over the currently available techniques and apparatus for performing these surgical techniques.

SUMMARY OF THE INVENTION

The method and device of the present invention facilitates the procedure of a transverse osteotomy of both ilia and a secondary osteotomy through the pelvic symphysis. A plate is utilized which has facility for attachment of eight screws into the animal bone tissue to hold the plate in place more securely, and which prevents broken, loosened screws and the loss of bone purchase. In addition, the shape of the plate represents a significant advance over prior art plates and has several important characteristics. First, only one side of the plate has sharply angled surfaces to accommodate rotated pelvic bone portions. The other side of the plate is flat and facilitates a more stable direct insertion of the bone screws. The flatness and the provision of chamfers which allow the screws to enter the bone at an angle perpendicular to the bone surface reduces the torque and spreads the holding forces. Any angling of the outside of the plate causes non-even pressure to be applied to the bores provided for insertion of the bone screws. In the configuration of the present invention, the bores can closely match the shapes of the heads of the bone screws and provide less exposed material at the outside of the plate.

Even more important is the ability to bend, or even torque the plate. Since one side of the plate is solid, more than ample material is provided to enable the plate if needed to be twisted along its axis, if needed, and to further bend the plate along its axis to better provide for the ability to insert bone screws at right angles to the extent of the pelvic bone tissue, if needed. From a perspective looking down onto the top of the pelvis, a straight plate would force the bone screws to be inserted at an angle with respect to the plate in order to achieve right angled bone insertion, or where the bone screws are inserted straight into the plate, would result in the bone screws insertion into the bone tissue at an angle which would weaken the attachment of the plate.

BRIEF DESCRIPTION OF THE DRAWINGS

The invention, its configuration, construction, and operation will be best further described in the following detailed description, taken in conjunction with the accompanying drawings in which:

FIG. 3 is a perspective view of the plate of the present invention and showing all angles and edges in the plate with the use of dashed lines;

FIG. 4 is a view taken along line 4—4 of FIG. 1 and illustrating the direct insertions of the bone screws into the place and the mating of the screw heads with chamfered bores in the plate;

FIG. 5 is a view taken along line 5—5 of FIG. 1. identifying information will be impressed;

FIG. 9 is a perspective view of a bending tool having triangular spaces to accept the end of the plate of the present invention and to allow bending and twisting of the plate;

FIG. 10 is an end view of two of the tools shown in FIG. 9 connected to a plate with arrows illustrating the application of twisting or torquing forces;

FIG. 11 is a side view of the two tools and plate shown in FIG. 10 but with arrows illustrating the application of bending forces along the length of the plate; and FIG. 12 is an exploded view of the two tools and plate as shown in FIGS. 10 and 11 and illustrating the manner of engagement of the triangular spaces of the tools to the ends of the plate.

DETAILED DESCRIPTION OF THE PREFERRED EMBODIMENT

Figure 1:
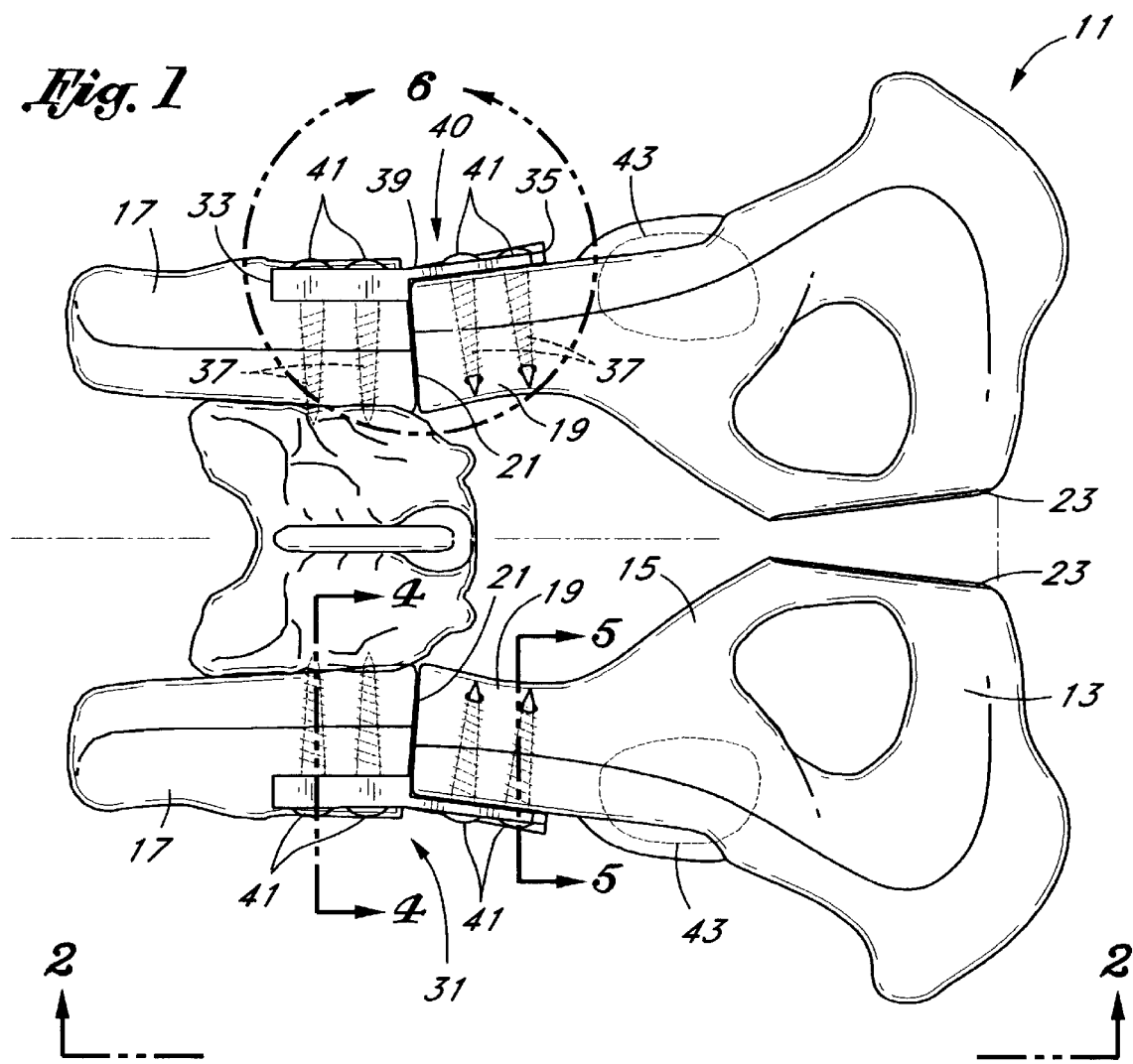
FIG. 1 is a top view of a canine pelvis which has undergone a transverse osteotomy of both ilium and a secondary osteotomy through the pelvic symphysis and in which the ilium are rejoined with the plate of the present invention.

The description and operation of the invention will be best described with reference to FIG. 1. FIG. 1 is a top view of a canine pelvis 11, and illustrates the tuber ischii 13, pubic ramus 15, and a rearward portion of the ilium 17, and a forward portion of the ilium 19 closer to the pubic ramus 15.

As can be seen, both ilium have been subjected to an ostomy along a plane 21 which separate the rearward portion 17 from the forward portion 19. Another ostomy along a plane 23 has been made through the pelvic symphysis and the areas of the bone surfaces along both of the planes 21 and 23 are exposed due to the rotation of the portions of the pelvis 11 from the forward portions 19 and connected bone structures.

As can be seen, each of the ilium are rejoined with a plate 31. From the angle of FIG. 1, the rear end of the plate 31 shows a relatively larger area top end surface 33, while the front end of the plate 31 shows a relatively smaller top end surface 35. The plate 31 is secured with eight bone screws 37, although only four bone screws 37 are seen since they overlie the other four bone screws 37. The bone screws 37 need not be of equal length and may be chosen to correspond to the depth of bone tissue to be penetrated.

The plate 31 will enable the separate securing of each bone segment with four bone screws 37 in order to provide additional support and strength. Each of the bone screws is expected to penetrate or come close to penetrating two surfaces of bone tissue. Six penetrations represent the minimum holding force necessary for successfully holding the plate. However, a real possibility exists in each procedure, of encountering damaged bone, soft cancellous bone tissue or cracks to the bone structure which destroy the holding power of a single bone screw 37.

The Association for Study of Internal Fixation (ASIF) has adopted guidelines for internal fixation as a function of bone plane penetration. A single screw which extends into and out of a volume of bone tissue crosses the cortex of the bone twice. For fixation on a single bone segment, and for cortical bone, 6 cortical penetrations, or three screws are the minimum which are required. Since the portions of the pelvis supporting the plate 31 are made of the much softer cancellous bone, the minimum number of penetrations would ideally be more than six, such as 7 or 8, requiring more than 3 screws. By providing the ability to use a fourth bone screw 37, the plate 31 of the present invention severely diminishes the chances of failure of the plate to hold the bone in place, and exceeds the minimum number of penetrations necessary to hold the plate 31.

Note that plate 31 would fit on the right side of the pelvis 11 of a canine. The plate which fits on the left side of the pelvis 11 of a canine is a plate 40 shown at the top of the FIG. 1. Further views of the plates 31 and 40 will illustrate that either of the plates may be turned in the vertical plane 180° and still have the same configuration. However, a left side plate 40 cannot be equivalently substituted for a right side plate 31. Hereafter, with respect to all characteristics other than left or right orientation, reference to plate 31 is equivalent to plates 31 or 40.

Note that an outside surface 39 of the plate 31 is a continuous, generally smooth surface except for the gentle bow-type bending which occurs along the length of the plate 31. This bending is expected to be from about 10° to about 35°, but preferably from about 15° to about 30°.

Moreover, and as will be shown, it is expected that the veterinary surgeon will be called upon to modify the plate during or before surgery to "customize" the plate to a particular animal. Where tomographic scans are available, the angle of bend and twist may be largely either accomplished or pre-selected before surgery. Once the bone tissue of the rotated acetabular segment is finally assessed, the surgeon can make final changes to the angle of bend and amount of twist to which the plate 31 will be subjected before it is finally affixed to the canine pelvis.

Referring again to FIG. 1, the plate 31 is bowed about the midpoint of its length. Note that the bowed nature of the plate 31 enables the lengths of the bone screws 37 to be more nearly oriented at right angles with respect to the axis of the bone tissue of the ilium for both the rearward 17 and forward 19 portions of the ilium.

In terms of size, the plate 31 is expected to vary with the size of the canine pelvis 11 being secured. Larger canines will require larger plates 31 and smaller canines will require smaller plates 31. For the medium size canine, the plate 31 is expected to be about 1.5 to about 2.0 inches long and have a width of from about 0.3 inches to about 0.8 inches.

Above the outside surface 39 of the plates 31, the upper surfaces of heads 41 of the bone screws 37 are seen. The heads 41 barely rise above the outside surface 39 of the plate to form a more compact and integrated structure and to minimize interference with adjacent tissues once the procedure is completed. As will be seen, specialized, angled chamfering contributes to the low profile of the heads 41 of the bone screws 37.

Figure 2:
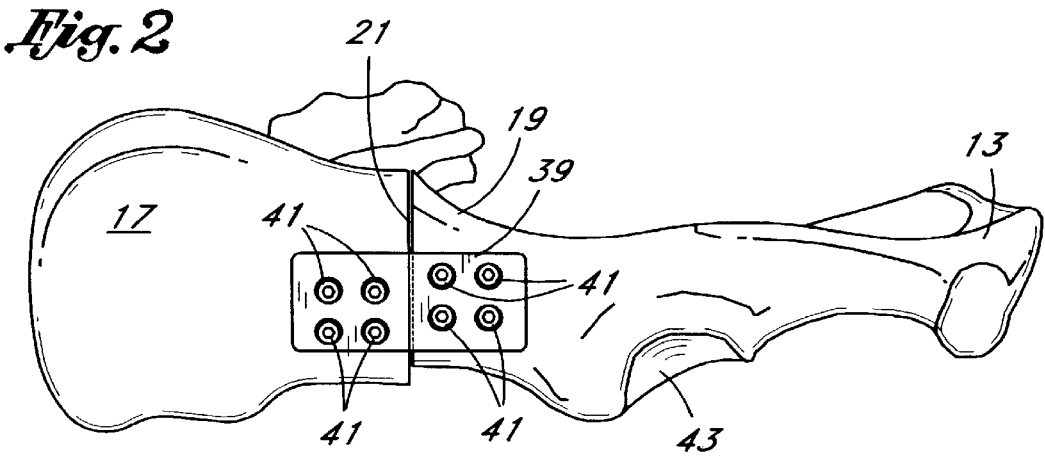
FIG. 2 is a side view of the view in FIG. 1 and taken along line 2—2 of FIG. 1.

Referring to FIG. 2, a side view taken along line 2—2 of FIG. 1 shows the position of the plate 31 with respect to the pelvis 11. The plane 21 is more clearly seen in alignment with the stepped separation surfaces of the plate 31 to be discussed.

Referring to FIG. 3, an enlarged view of the plate 40, which is the left side plate enables illustration of other specific aspects of the plate 40. This also applies to plate 31, but plate 31 has oppositely oriented surfaces as will be shown. A first end surface 45 is in the shape of a trapezoid and a second end surface 46, which is also in the shape of a trapezoid, faces away from the observer in FIG. 3. A pair of bottom end surfaces including a larger bottom end surface 47 and a smaller bottom end surface 49 mirror the larger top end surface 33 and smaller top end surface 35. If the plate 40 were flipped about its midpoint 180° the plate 40 would appear the same and the larger bottom end surface 47 would occupy the space and location of the larger top end surface 33.

Between the smaller top end surface 35 and the larger bottom end surface 47 is an upwardly inclined plane surface 51. Similarly, between the larger top end surface 33 and the smaller bottom end surface 49 is a downwardly inclined plane surface 53. If the plate 51 were rotated in a vertical plane about its midpoint 180°, the inclined plane surfaces 53 and 51 would have changed places, but would present the same orientation.

If it were plate 31 shown in FIG. 3, the relationship of the plane surfaces 51 and 53 would be opposite. If it were plate 31, the end surface 45 shown would have the smaller end of the trapezoid pointing downward, and the pair of bottom end surfaces would include a larger bottom end surface 47 at the left and a smaller bottom end surface 49 on the right. Further, the upwardly inclined plane surface 51 would be to the left and the downwardly inclined plane surface 53 would be to the right. As such it can be seen that the plates 40 and 31 have different orientation and except for such orientation are identical.

The inclined plane surfaces 53 and 51 each support a series of four bores 55. The bores 55 are perpendicular to the inclined plane surfaces 53 and 51, and for an important reason. It is the inclined plane surfaces 53 and 51 which will directly contact and support the bone tissue. Since the acetabular segment will be rotated it will have a different angle than the non-rotated segment and the differing angles of the inclined plane surfaces 53 and 51 enable the bracket 31 to closely contact and support the area of bone tissue of the portions of the ilia 19 adjacent to the inclined plane surfaces 53 and 51. As will be seen, the other end of the bores 55 are chamfered to accommodate the heads 41 of the bone screws 37. The outer portions of the bone tissues which the plane surfaces 51 and 53 contact will be oriented to as closely as possible approximate the angular differences of the orientation of the plane surfaces 51 and 53. Pursuant to this goal, it is acceptable to both bend and torque the plate 31 about its length in order to have some customizing effect upon the plate 40.

This ability is not possible with a plate having a pair of non-parallel planar surfaces joined by a web at right angles to the plane of the plates. This is because the web creates two separate corners having non-parallel bending axes, and the bending will occur predominately along those corners causing one of the plate portions to angle up and the other to angle down. Torquing a plate having a pair of non-parallel planar surfaces joined by a web at right angles to the plane of the plates is simply out of the question. Since the web has a planar extent in the direction of rotation, it will be absolutely resistive to force, leaving the plate portions to unevenly distort.

The junction where the inclined plane surfaces 53 and 51 intersect leave no space between those surfaces and is shown as intersect plane 57. The intersect plane 57 includes a triangular surface 61 at the side of downwardly inclined plane surface 53, and a triangular surface 63 at the side of upwardly inclined plane surface 53, which faces away from the viewer as seen in FIG. 3. The opposing apex of each triangular surface 61 and 63 are virtually continuous, resulting only in a 180° change of orientation in moving from one triangular surface to the other.

From the first end 45 to the second end 46, and extending across the mid line of the surfaces 51 and 56, a continuous surface line can be drawn. Since the plate 40 is curved, the resulting theoretical continuous midline surface line is curved. Since the outside surface 39 is generally continuous and smooth, the curvature of the plate 40 will produce a gentle curvature over the outside surface 39 and this gentle curvature is seen in FIG. 1 on both the plates 31 and 40.

The abutting construction of the surfaces 51 and 53 insures that the center of the plate 40 will be more than adequately strong enough to accept any torquing forces or further bending forces along which the veterinary practitioner needs to make at the time of surgery to insure a better fit, but without loss of strength. Since one half of the plates 31 and 40 have their weaker areas at the narrower top end surface 35, while the other half of the plates 31 and 40 have their weaker areas at the narrower bottom end surface 49, and since the middle of the plates 31 and 40 will present the weaker area of bending along a straight longitudinal line, the somewhat angular apex for the angle α is correct, so long as the torsion is controlled during bending.

As can also be seen in FIG. 3, the plate 40, (as will plate 31) is bent along its length along an angle α which may be from between about 3° to about 15°. In addition, although described as an angle, the bend need not be place sharply about an axis. The plate 40 or 31 may be bent to achieve a gentle curvature, and approach the angle α as taken from lengths of the plate 31, 40 nearer its ends.

Referring to FIG. 4, a view taken along line 4—4 of FIG. 1 gives a sectional view looking into the rearward portion of the ilium 17, and which shows the forward portion of the ilium 19 behind it. The curvature of the outside portion of the plate 31 can clearly be seen. Seen for the first time are the chamfers 65. From the bore 55 which opens to the chamfer 65, an accommodation bore 66 is seen which accommodates the head of the heads 41 of the bone screws 37. Also shown is the hexagonal space 67 which is used to key the bone screws 37 to enable them to be driven in with a hex key or similar tool. The use of a hex key driver, along with the low profile of the heads 41 within the chamfers 65, contributes to the lower, smoother profile which will be less damaging to surrounding tissues. Notice how the bores 55 combine with the chamfers 65 to keep the bone screws 37 extending into the rearward portion of the ilium 17 in an orientation perpendicular to the outer surface of the bone tissue opposing the plate 31 line. FIG. 4 is a vertical section, and reference may be had back to the FIG. 1 to illustrate the fact that the bone screws 37 enter the ilial sections at right angles with respect to the outer surface of the bone tissue in order to give maximum holding force. Even more important, FIG. 4 dramatically illustrates the differences in angular position of the rotated and un-rotated ilial sections 17 and 19 respectively, which must be supported by the plate 31, and also by the plate 40 if the view were taken from the other side.

Referring to FIG. 5, a view taken along line 5—5 of FIG. 1 illustrates the fit of the portion of the plate 31 forward of the rearward portion 17. Further chamfers 65 can be seen.

Although the present invention has been drawn to a pair of plates 31 and 40 which adequately support the canine pelvis after performing a transverse osteotomy of both ilium and a secondary osteotomy through the pelvic symphysis, the plate can be used in any circumstance where cut and rotated bone segments are to be supported in an angular relationship to each other. Although the physical dimensioning of the plates 31 and 40 indicate a proper size for the small canine pelvis 11, it is understood that the principles embodied in the plates 31 and 40 can be utilized in other mammals and in humans with appropriate adjustment in the plates to take account of bone size and bearing load, bone configuration, fastener strength and the extent to which resort must be had to fastening structures.

Figure 6:
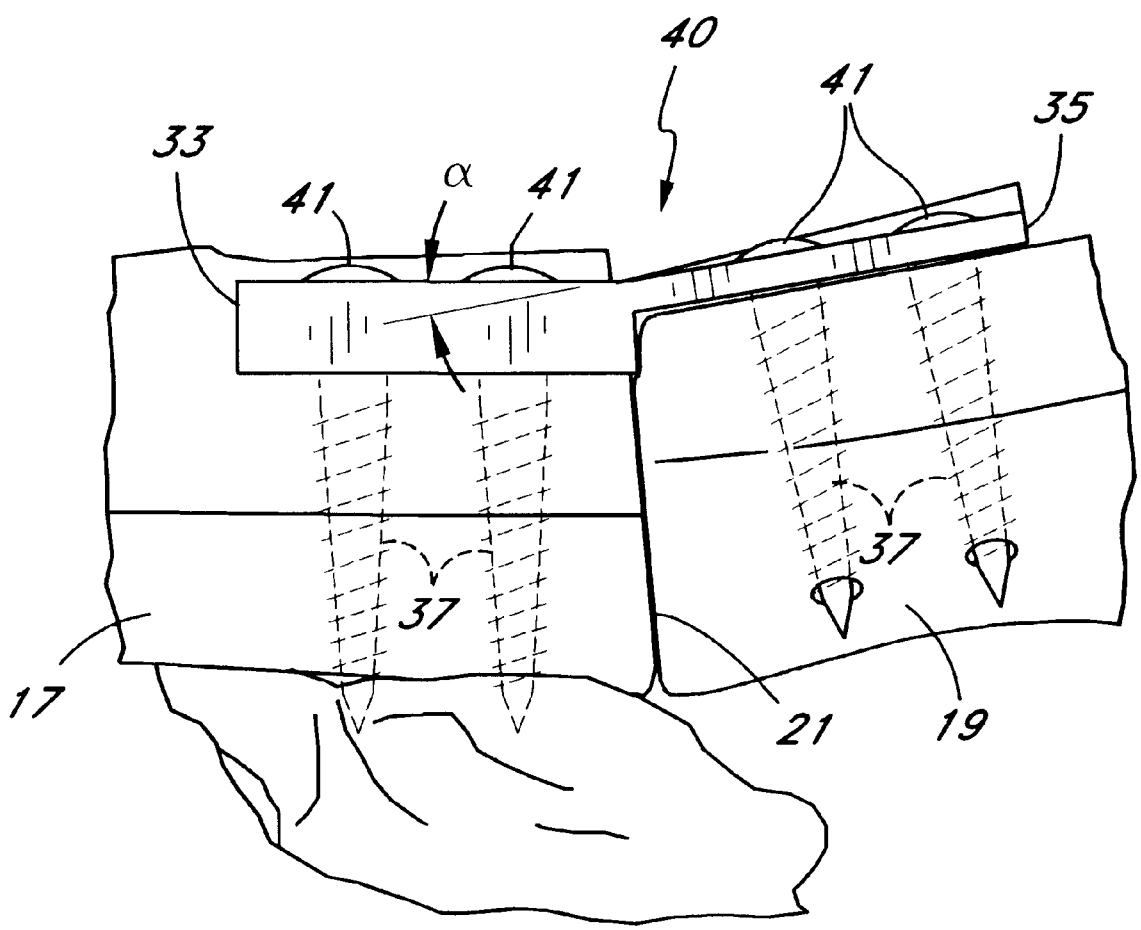
FIG. 6 is an enlarged view taken along line 6—6 of FIG. 1.

Referring to FIG. 6, a top view taken about line 6—6 of FIG. 3 illustrates a closeup view of the structures shown. As can be seen, in some cases the bone screws 37 may protrude through the bone material of the ilium 19, and this normally be expected to occur. Again, the angle α is shown to provide a better visual reference. From the top view of FIG. 6, the bone screws 37 are again shown to enter the rearward portion of the ilium 17, and the forward portion of the ilium 19 at right angles to the surface of bone tissue opposing the plate 40.

Figure 7:
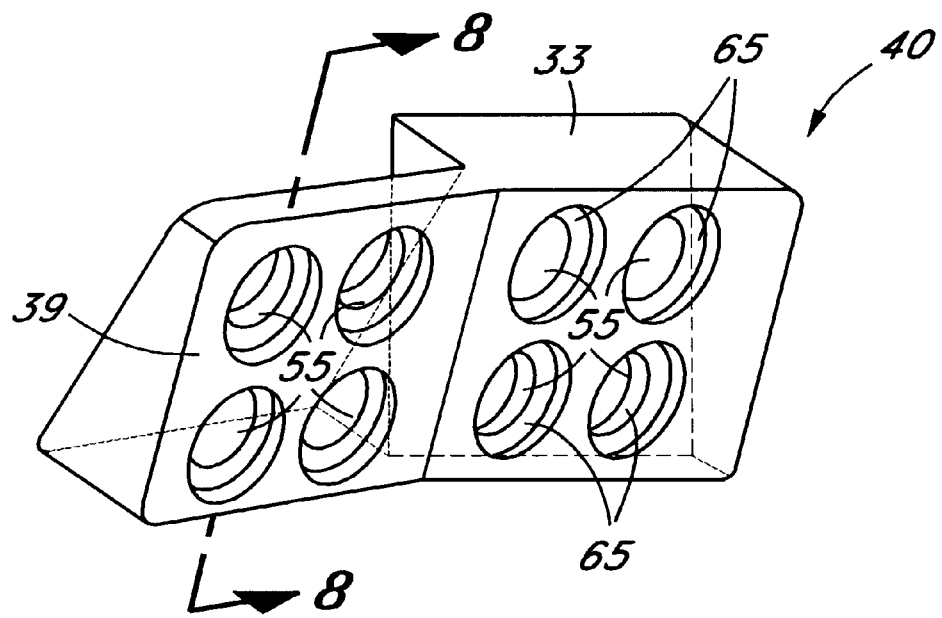
FIG. 7 is a rear view of the plate of the invention and illustrating the bores, their chamfered surfaces and accommodation bores opening to the smooth side.

Referring to FIG. 7, a view of the outside of the plate 40 again illustrates the four bores 55 in each half of the plate 40 behind it. The chamfers 65 as seen, but will be shown in greater detail. The surface 39 is seen in total for the first time.

Figure 8:
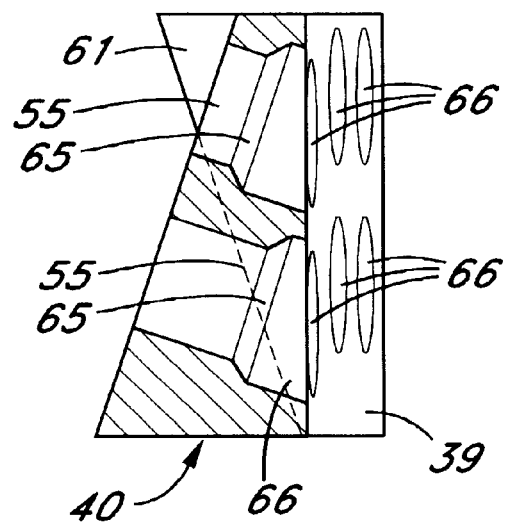
FIG. 8 is a sectional view taken along line 8—8 of FIG. 7 and illustrating a cross sectional view of the bores seen in FIG. 7.

Referring to FIG. 8, a view taken along section 8—8 of FIG. 7 illustrates a view taken through the vertical center of the first two bores 55 and chamfers 65 at the end of the plate 40. As can be seen, the bore 55 opens into a chamfer 65 and then into the screw head accommodation bores 66. The curvature of the plate 40 can also clearly be seen and the outside of the other accommodation bores 66 can be partially seen.

The bending of the plates 31 and 40 will, all other things being equal, attempt to be accompanied with some slight torsion. Since the plates 31 and 40 are relatively small, some mechanism must be available to allow the veterinary surgeon to adjust the plates easily before and during surgery. Pliers and wrenches are unacceptable since they are not customized to the shape and size of the plates 31 and 40 and would tend to be scratched, burred and damaged by such general use implements. Further, since much of the manipulation of the plates 31 and 40 may occur during surgery, general use implements of this type would either be non-sterile, or difficult to sterilize if complex.

Referring to FIG. 9, a bending tool 71 is illustrated in side profile. Tool 71 has a first "L" shaped end 73 and a second "L" shaped end 75, joined by a common handle 77. At each of the ends 73 and 75 is a triangular space 79 which may or may not constitute a through bore. The use of a triangular space 79 will enable the use of the tool 71 with different width plates 31 and 40. Wider plates 31 and 40 will taper to a narrower width.

The simplicity of the tool 71, having no moving parts or hidden surfaces makes it easier to sterilize. The triangular space 79 at the end 73 is preferably of a different size than the triangular space 79 at the second end 75 Beginning with FIG. 10, an example of how the tools 71 are used to shape the plates 31 and 40 is shown. In FIG. 10, the end 75 and its triangular space 79 of a tool 71, to the left, engages one end of a bracket 31, while the end 75 and its triangular space 79 of another tool 71, to the right, engages the other end of a bracket 31. The motion which is depicted by the arrows indicates a torquing of the bracket 31.

Referring to FIG. 11, a bracket 40 is engaged in a manner similar to that of bracket 31 and the arrows on the tool 71 indicate a bending of the bracket 40 along its length to increase its angle of bend. Due to the length of the handles 77, the brackets 31 and 40 can be easily manipulated by the veterinary surgeon during an operation to give optimum fit. The brackets 31 and 40 may be compared with the shape and configuration of the rearward and forward portions of the ilium 17 and 19 and can be adjusted to correct for any unexpected configurations or to compensate for any miscalculations.

Referring to FIG. 12, an exploded view of the bottom of FIGS. 10 and 11 are shown. Here, the bracket 31 is engaged by the bottom ends 75 of the tools 71 in the triangular spaces of the tools 71. As can be seen, each end of the bracket 31 is sufficiently covered such that it is securely grasped and the torsional forces and bending will be well distributed throughout the body of the bracket 31.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. In the field of pelvic osteotomy a fixation plate used to orient two cut and separated ilial sections, and comprising:

an elongate plate having a first and a second end and having a first side defining a pair of adjacent angularly tilted surfaces and wherein each one of said pair of adjacent angularly tilted surfaces forms a frustrated wedge with respect to said second side of said fixation plate, said elongate plate defining a curved surface line extending from said first to said second end and continuously across said pair of adjacent angularly tilted surfaces, said plate also having a second side oppositely disposed from said first side.

2. In the field of pelvic osteotomy a fixation plate used to orient two cut and separated ilial sections, and comprising:

an elongate plate having a first and a second end and having a first side defining a pair of adjacent angularly tilted surfaces, and wherein each of the pair of adjacent angularly tilted surfaces defines a pair of bores having axes normal to said angularly tilted surfaces and wherein one of said pair of bores has an axial length longer than the other one of said pair of bores, said elongate plate defining a curved surface line extending from said first to said second end and continuously across said pair of adjacent angularly tilted surfaces, said plate also having a second side oppositely disposed from said first side.

3. The fixation plate of claim 2 where said curved line is convex with respect to said first side of said plate.

4. The fixation plate of claim 2 wherein said pair of adjacent angularly tilted surfaces defining said curved surface line are also curved, but discontinuous where said pair of angularly tilted surfaces abut transition from one to the other away from said curved surface line.

5. The fixation plate of claim 2 wherein each of the bores has a first end adjacent an associated said angularly tilted surface and a second end more closely adjacent said second surface and wherein each bore has a chamfer directed toward said second surface of said plate.

6. The fixation plate of claim 5 wherein each chamfer lies adjacent a screw head accommodation bore opening to said second surface of said plate.

7. The fixation plate of claim 2 wherein said second side of said fixation plate has a concave curvature.

8. The fixation plate of claim 2 where said bores each have a chamfer opening to said second side of said fixation plate.

9. The fixation plate of claim 2 wherein said curved surface line has an angular displacement of from about 10° to about 30°.

10. In the field pelvic osteotomy a fixation plate used to orient two cut and separated ilial sections, and comprising:

an elongate plate having a first and a second end and having a first side defining a pair of adjacent angularly tilted surfaces and defining a curved surface line extending from said first to said second end and continuously across said pair of adjacent angularly tilted surfaces, said plate also having a second side oppositely disposed from said first side and wherein each of the pair of adjacent angularly tilted surfaces defines four bores having axes normal to said second side of said plate, and wherein two of said four bores of each one of said pair of angularly tilted surfaces have axial lengths longer than the other two of said four bores of each one of said pair of angularly tilted surfaces.

11. The fixation plate of claim 10 wherein the axes of any two of said bores having substantially the same axial length are not parallel to the axes of any other two bores having substantially the same axial length.

12. The fixation plate of claim 10 where said curved line is convex with respect to said first side of said plate.

13. The fixation plate of claim 10 wherein said pair of adjacent angularly tilted surfaces defining said curved surface line are also curved, but discontinuous where said pair of angularly tilted surfaces abut transition from one to the other away from said curved surface line.

14. The fixation plate of claimm 10 wherein said second side of said fixation plate has a concave curvature.

15. The fixation plate of claim 10 where said bores each have a chamfer opening to said second side of said fixation plate.

16. The fixation plate of claim 10 wherein said curved surface line has an angular displacement of from about 10° to about 30°.

17. A fixation plate bending and torquing tool comprising:

an elongate handle having a first end and a second end, and having a triangular space adjacent one of said first and second ends to accept an end of a fixation plate to enable bending and torquing said fixation plate.

18. A fixation plate bending and torquing tool as recited in claim 17 wherein both said first and said second ends have a triangular space adjacent an associated one of said first and said second ends.

19. In the field of pelvic osteotomy a procedure on an animal pelvis comprising the steps of:

making a triangular separating cut in a pelvic symphysis such that subsequent rotation of the ilial sections can be accomplished without overlap or interfering contacts of a remaining portion of the pelvic symphysis;

making an osteotomy on each of a pair of ilia of said animal pelvis to form a pair of forward ilial sections separated from a pair respectively associated rear ilial sections, the plane of each said osteotomy perpendicular to an axis of rotation of each of said forward ilial section;

rotating each forward ilial section adjacent its associated rear ilial section; and joining each forward ilial section to its associated rear ilial section with a fixation plate comprising:

an elongate plate having a first and a second end and having a first side defining a pair of adjacent angularly tilted surfaces and defining a curved surface line extending from said first to said second end and continuously across said pair of adjacent angularly tilted surfaces, said plate also having a second side oppositely disposed from said first side.

20. The procedure as recited in claim 19 wherein said pair of adjacent angularly tilted surfaces has a plurality of bores having axes perpendicular to said angularly tilted surfaces and wherein said joining step is accomplished by securing a plurality of bone screws, each inserted through an associated bore and into the forward and rear ilial sections.

* * * * *